United States Patent [19]

Sibley

[11] 4,276,886
[45] Jul. 7, 1981

[54] BLOOD PRESSURE RECORDER

[76] Inventor: Alfred E. Sibley, Box 432L, Rte. 1, Boulder Creek, Calif. 95006

[21] Appl. No.: 70,076

[22] Filed: Aug. 27, 1979

Related U.S. Application Data

[63] Continuation of Ser. No. 842,203, Oct. 14, 1977, abandoned.

[51] Int. Cl.³ .............................................. A61B 5/04
[52] U.S. Cl. .................................... 128/681; 128/900
[58] Field of Search ..................... 128/677, 680–682, 128/900

[56] References Cited

U.S. PATENT DOCUMENTS

| | | | |
|---|---|---|---|
| 1,906,806 | 5/1933 | Plesch | 128/677 |
| 2,186,517 | 1/1940 | Bradford | 128/677 |
| 2,447,018 | 8/1948 | Keinath | 128/680 |
| 3,754,545 | 8/1973 | Weinstein | 128/682 |

Primary Examiner—William E. Kamm
Attorney, Agent, or Firm—John L. McGannon

[57] ABSTRACT

Apparatus for measuring and recording a patient's blood pressure at various times throughout the day while the patient is unattended, wherein the apparatus includes a circular disk chart and a marking pen having a tip adjacent but normally spaced from one face of the disk. The marking pen is pivotally mounted for movement across the face of the disk in a radial direction and the marking pen is moved in the radial direction when a pressure cuff is inflated on a limb, such as an arm, of the patient. A diaphragm assembly coupled to the cuff is mechanically connected to the marking pen to cause it to pivot in one direction as the cuff is inflated. A microphone carried by the cuff detects Karotkoff sounds as the cuff is deflated. The pulses sensed by the microphone are amplified and used to actuate a driver which energizes a solenoid to attract the marking pen, causing the marking pen to be momentarily moved into engagement with the chart to form dots therein corresponding to the Karotkoff sounds between the systolic and diastolic pressures. A switch responsive to the pivotal movement of the marking pen enables the amplifier and solenoid driver when the cuff is inflated.

5 Claims, 2 Drawing Figures

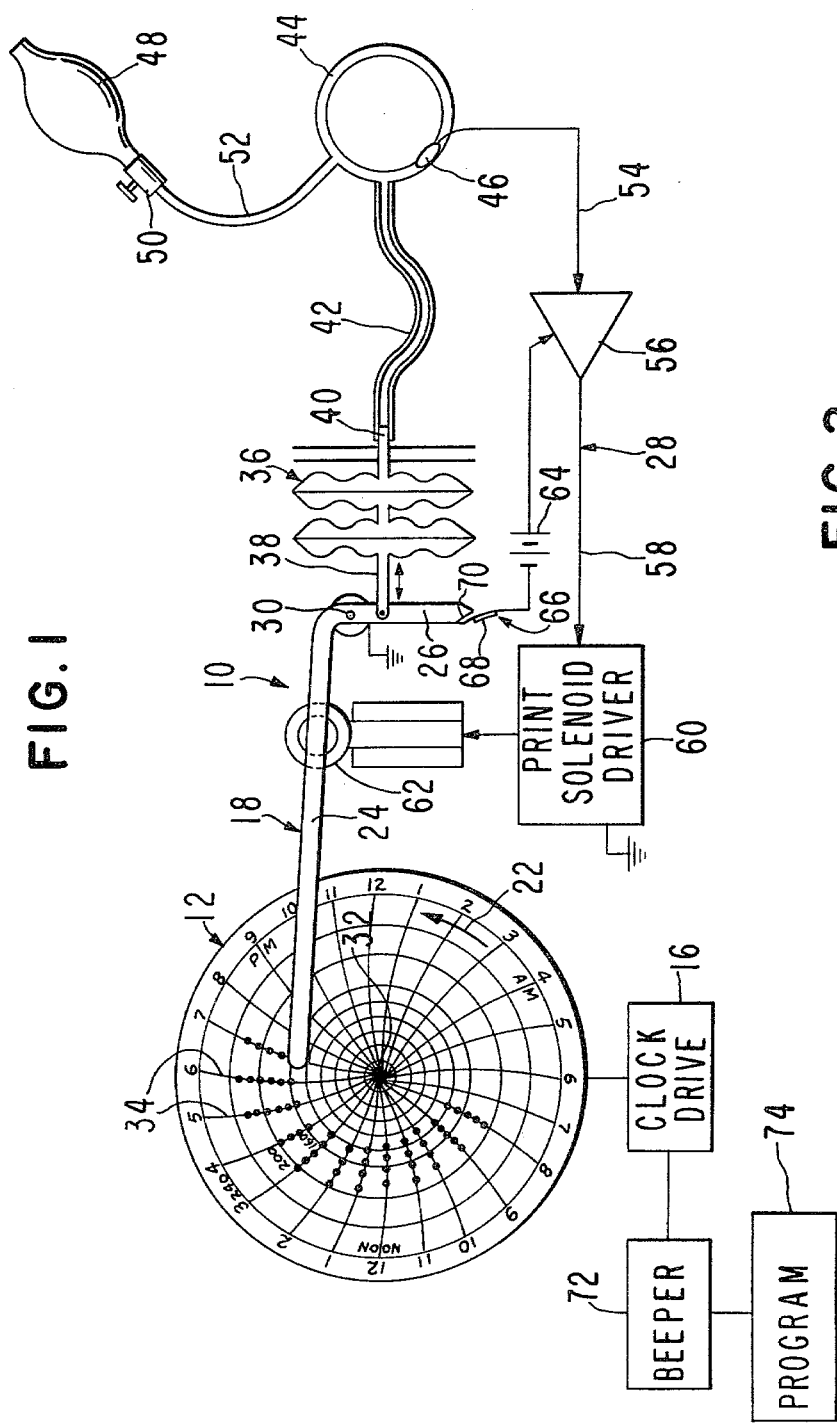
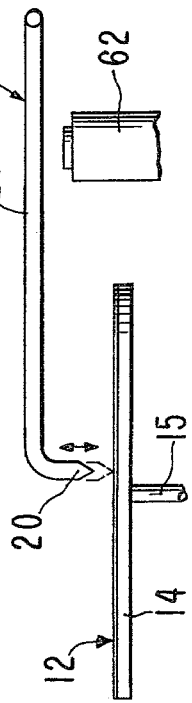
FIG. 1
FIG. 2

BLOOD PRESSURE RECORDER

This is a continuation of application Ser. No. 842,203, filed Oct. 14, 1977 now abandoned.

This invention relates to improvements in the measurement of blood pressures of humans and, more particularly, to apparatus permitting a patient to automatically measure and record his own blood pressure.

BACKGROUND OF THE INVENTION

It is often desirable for a patient to be able to monitor his own blood pressure throughout certain times of the day. This is especially important for a cardiac patient who must obtain specific blood pressure data when he feels certain symptoms coming on so that a physician can later review the data to determine the progress of the patient by correlating a description of the symptoms with the blood pressure measurements.

A number of attempts have been made to provide apparatus to allow a patient to take his blood pressure readings at different times throughout a day or a period of several days. The following U.S. Patents disclose blood pressure recorders, none necessarily for use by unattended patients: Nos. 1,934,124; 2,186,517; 2,447,018; 2,989,051; 3,557,779 and 3,623,478. Of these patents, U.S. Pat. No. 3,557,779 probably is the most pertinent with respect to a patient taking his own blood pressure. However, this patent reveals a device which is to be carried entirely on the limb, such as the arm of the patient, and is required to be so compact that accuracy and ease of operation must be sacrificed, thereby limiting the credibility of the results obtainable with the use of the device. The other patents disclose structures which are relatively complex and would require an additional person in attendance to operate them. These patents disclose single measurement devices and are not intended to be used by ambulatory patients where it is necessary to record and store a series of measurements.

As a result of the limitations of prior devices mentioned above, a need has arisen for an improved blood pressure recorder which permits a patient to automatically take and record his own blood pressure in a manner such that the blood pressure readings throughout various intervals in a day or period of several days can be readily analyzed for diagnostic or other purposes.

SUMMARY OF THE INVENTION

The present invention is directed to an improved blood pressure recorder which satisfies the aforesaid need, wherein the recorder includes apparatus which permits a patient unattended by a physician or other persons to measure and record his own blood pressure automatically at any time so that the readings will be displayed on a chart or record, such as a circular disk chart, which shows the times when the readings were taken. The apparatus of this invention is operated by the patient solely by inflating and deflating a pressure cuff typically worn continuously on the arm of the patient during the period in which a number of blood pressure measurements are to be taken, such as during a 24-hour period. The resulting measurements are recorded and stored in a manner such that an attending physician, who need not be present when the device is used, can later review the recorded measurements and determine the progress of a patient's recovery during the period covered by the readings.

To this end, the present invention includes a shiftable record capable of being marked, such as a circular disk chart, on which the blood pressure measurements are to be recorded and stored permanently. A marking pen in the form of an elongated arm is pivotally mounted for movement in a direction transverse to the direction of movement of the record with the tip of the marking pen normally out of engagement with the disk record but movable into marking relationship therewith when a microphone carried by a pressure cuff detects Karotkoff sounds. These sounds are amplified and used to energize a solenoid which attracts the arm and moves its tip momentarily into engagement with the disk chart to form a series of dots thereon which extend along a line transversely of the direction of movement of the record. Each series of dots represents the blood pressures between the systolic and diastolic pressures for a particular time of a recording period, such as a 24-hour recording period, the record being calibrated in terms of time in the direction of movement of the record and calibrated in terms of pressure in the direction of movement of the arm. The apparatus also has means for enabling the electrical circuitry thereof only when the pressure cuff is inflated to thereby avoid current drain on the voltage source for the circuitry.

The primary object of this invention is to provide an improved blood pressure recorder which can be operated by a patient without anyone else in attendance yet the only act required of the patient is the inflation and deflation of a pressure cuff on a limb of the patient so that blood pressure readings can be taken automatically at different intervals throughout a certain recording period.

Another object of this invention is to provide a blood pressure recorder of the type described, wherein a permanent record of blood pressure readings at different intervals can be made yet the recorder is simple and rugged in construction, is extremely easy to operate and can be carried by the patient at all times of the day while it provides data for later use by an attending physician.

Other objects of this invention will become apparent as the following specification progresses, reference being had to the accompany drawings for an illustration of the invention.

IN THE DRAWINGS:

FIG. 1 is a schematic view of the blood pressure recorder of this invention showing a pivotal arm for making individual marks on a circular recorder; and FIG. 2 is a side elevational view of the arm and the record chart to illustrate the way in which the arm pivots in a second direction.

The blood pressure recorder of the present invention is broadly denoted by the numeral 10 and includes a record or chart formed from paper disk 12 mounted on a rotating platen 14 (FIG. 2) whose shaft 15 is rotatably driven by a clock drive 16. Disk 12 is calibrated in millimeters of mercury in the radial direction and in real time units in a circumferential direction as shown in FIG. 1. Thus, clock drive 16 continuously rotates platen 14 and thereby disk 12. The central axis 32 of disk 12 is typically vertical.

A marking pen 18 has a marking tip 20 (FIG. 2) directly adjacent disk 12 and normally spaced therefrom. Marking pen 18 includes an elongated arm 24 which has a right angle bend at one end thereof to form tip 20 and a right angle bend at the opposite end to form a segment 26. Tip 20 is in a plane substantially perpendicular to the plane of segment 26. Segment 26 is electrically conductive so as to form part of a circuit 28 hereinafter described.

Arm 24 is pivotally mounted by a pin 30 for rotation about an axis substantially parallel with the central axis 32 of disk 12. Pin 30 is located a sufficient distance from disk 12 and arm 24 has a length sufficient to permit the tip 20 of arm 24 to transverse a slightly curved path denoted by line 34 each time the arm pivots relative to disk 12 about the axis of pin 30.

Although tip 20 is normally out of engagement with disk 12 as shown in full lines in FIG. 2, the tip is movable momentarily into engagement with the face of disk 12 to form a mark or dot thereon, tip 20 having marking means (not shown), such as a felt tip pen element or the like. Arm 24 is sufficiently long and slightly resilient to allow tip 20 to move into the dashed line position of FIG. 2 as arm 24 is pulled downwardly by a force hereinafter described. In the alternative, a pivot means (not shown) in addition to pivot pin 30 can be provided near pin 30 to allow arm 24 to pivot toward disk 12 so that tip 20 can engage the face of the disk. The disk is moving slow enough and the tip only engages it for a few milliseconds so that a dot is formed rather than a line as the tip engages the disk.

Means for pivoting arm 24 about the axis of pin 30 comprises a diaphgram assembly 36 having an arm 38 pivotally coupled to segment 26 between the ends thereof. Assembly 36 has a fluid inlet 40 coupled by a flexible tube 42 to a blood pressure cuff 44 having a built-in microphone 46 for detecting Karotkoff sounds. An inflating bulb 48 having a valve 50 is coupled by a flexible tube 52 to blood pressure cuff 44 to inflate the latter when the bulb is squeezed.

Microphone 46 is coupled by a lead 54 to a pulse amplifier 56 forming a part of circuit 28. The output of amplifier 56 is coupled by a lead 58 to a solenoid driver 60, the latter being coupled to a solenoid 62 which, when actuated, magnetically attracts arm 24 (FIG. 2) to cause tip 20 to move into the dashed line position in engagement with the face of disk 12. To effect this magnetic attraction, arm 24 is of a ferromagnetic material or has a small mass of such material attached to it.

Circuit 28 further includes a voltage source 64 and a switch 66 comprised of a spring arm 68 which normally engages an insulator 70 on the end of segment 26 when the arm is in an inoperative position near central axis 32 of disk 12. However, spring arm 68 will flex to the left when viewing FIG. 1 and then pass beneath segment 26 as arm 24 rotates in a clockwise direction, i.e., when diaphragm assembly 36 is inflated as cuff 44 is inflated. Then, arm 68 will engage another side of segment 26 and close circuit 28 which contains segment 26 and thereby enable amplifier 56 and solenoid driver 60.

In use, cuff 44 is inflated by a bulb 48 typically to a pressure of 240 mm. of mercury or other pressure prescribed by an attending physician. The time for taking a reading can be selected by the patient or his physician. Also, if the readings are to be taken periodically, a "beeper" alarm 72 operated by a program 74 can be used, if desired.

After cuff 44 has been inflated, pressure relief valve 50 is opened to allow the air to escape from the cuff at a controlled rate, usually around 5 mm. of mercury per second. As cuff 44 is inflated, switch 66 is closed and diaphragm assembly 36 expands to cause pivotal movement of arm 24 in a clockwise sense about the axis of pin 30 when viewing FIG. 1. Tip 20 will then move to a location near the outer periphery of disk 12.

As the air pressure in cuff 44 starts to fall, arm 24 starts to rotate in a counterclockwise direction and tip 20 moves toward the low range of the pressure scale, i.e., toward central axis 32 of disk 12. Switch 66 will continue to enable amplifier 56 and driver 60 as arm 24 is moved in a clockwise direction by the expansion of assembly 36. Thus, amplifier 56 and driver 60 continue to be enabled as tip 20 moves toward central axis 32.

When the pressure in cuff 44 reaches a value equal to the systolic pressure in the brachial artery. The Karotkoff sounds are successively produced by the mometary collapse of the artery. These sounds are detected by microphone 46 in the form of pulses which are amplified by amplifer 56. The output of the amplifier actuates driver 60 which, in turn, energizes solenoid 62 to attract arm 24 and cause tip 20 to move momentarily into marking engagement with disk 12 to form a dot thereon. A dot is provided for each successive pulse generated by microphone 46 and a number of groups of dots or marks are shown on various lines 34 on disk 12 as shown in FIG. 1.

When the diastolic pressure is reached, the Karotkoff sounds will cease and no further dots will be marked or applied on disk 12 as arm 24 continues toward the zero pressure or inoperative position thereof. As it does so, switch 66 is opened to disable circuit 28. The series of dots produced at each use of cuff 44 represents the systolic and diastolic pressures and the pressures therebetween for a specific time interval. Since the disk is mounted on a clock-driven rotating platen, each series of dots will appear at the time the pressure was taken. The clock drive will be sufficiently slow so that the dots will fall in alignment with each other on the disk.

I claim:

1. In a blood pressure recorder of the type having an inflatable cuff: a record capable of being marked; means mounting the record for movement in one direction; means coupled with the record for moving the same in said one direction; a marking device; first means mounting the marking device in spaced relationship to the record and for movement along a line adjacent to and spaced from the record, said line extending in a second direction transverse to said one direction, said first means permitting the marking device to move into and out of engagement with said record when the marking device is at any of a number of locations along a line extending in said second direction, whereby a dot is market on the record each time the marking device is shifted into engagement with the record as the marking device moves along said line; means coupled with said marking device for moving the same along a line extending in said second direction as a function of cuff pressure; electrically actuated means coupled with the marking device and responsive to Karotkoff sounds for shifting the marking device into and out of engagement with the record a number of times as the marking device moves along a line extending in said second direction, said shifting means including an electronic circuit for actuating said shifting means when the circuit is enabled; and means responsive to fluid pressure in said cuff for enabling said circuit, whereby a line of unconnected dots will be marked on the record at locations along a line extending in said second direction when the marking device is shifted into and out of engagement with the record.

2. In a blood pressure recorder as set forth in claim 1, wherein said record is a disk, said record mounting means being operable to rotate the disk about its central axis, said one direction extending circumferentially about said central axis and the second direction extending generally radially of said central axis.

3. In a blood pressure recorder as set forth in claim 1, wherein the mounting means for the marking device includes a structure allowing the marking device to pivot about a first axis in response to cuff pressure and about a second axis in response to the generation of Karotkoff sounds.

4. In a blood pressure recorder as set forth in claim 1, wherein said means for moving the marking device along a line extending in said second direction includes an assembly responsive to cuff pressure, said moving means including a circuit containing a driver, and a solenoid coupled with the marking device and actuated by the driver, the input to the circuit being electrical signals generated in response to Karotkoff sounds.

5. A blood pressure recorder comprising: a record in the form of a disk capable of being marked; means mounting the disk for rotation about its central axis in one direction; means coupled with the disk for rotating the same in said one direction; an arm having a marking device thereon at one end thereof; means mounting the arm for movement adjacent to the disk in a generally radical direction with reference to said central axis, said marking device being normally spaced from the disk, said mounting means permitting the arm to move toward and away from the disk to thereby permit the marking device to move into and out of engagement with the disk when the marking device is at any of a number of locations along a line extending radially of said central axis, whereby a dot is marked on the disk each time the marking device is moved into engagement with the disk; an inflatable pressure cuff adapted to encircle a body part; a microphone associated with the cuff and adapted to sense Karotkoff sounds and to form signal pulses corresponding thereto; means coupling said cuff with said arm for moving the latter radially and outwardly of said central axis in response to the inflation of the cuff, said arm being moveable generally radially and toward said central axis as the cuff deflates; and electrically actuated means coupled with the marking device and responsive to sign pulses from said microphone for shifting the arm toward the record to thereby shift the marking device into engagement with the disk a number of times as the arm moves radially toward the central axis, said shifting means including a circuit for actuating said shifting means when the circuit is enabled; and means responsive to fluid pressure in the cuff for enabling the circuit.

* * * * *